US011266847B2

(12) United States Patent
Christiansen et al.

(10) Patent No.: US 11,266,847 B2
(45) Date of Patent: Mar. 8, 2022

(54) MULTI-FUNCTION PORTABLE AUTOMATED EXTERNAL DEFIBRILLATOR

(71) Applicant: Black Diamond Creations, LLC, St. George, UT (US)

(72) Inventors: Brett D. Christiansen, St. George, UT (US); Christopher B. Christiansen, St. George, UT (US); James B. Christiansen, St. George, UT (US); Clancy B. Christiansen, St. George, UT (US); Candice S. Christiansen, St. George, UT (US); Bryce B. Christiansen, St. George, UT (US); Susan G. Christiansen, St. George, UT (US); Phillip Dietz, St. George, UT (US)

(73) Assignee: Black Diamond Creations, LLC, St. George, UT (US)

( * ) Notice: Subject to any disclaimer, the term of this patent is extended or adjusted under 35 U.S.C. 154(b) by 0 days.

(21) Appl. No.: 16/874,571

(22) Filed: May 14, 2020

(65) Prior Publication Data

US 2020/0360707 A1 Nov. 19, 2020

Related U.S. Application Data

(60) Provisional application No. 62/848,204, filed on May 15, 2019.

(51) Int. Cl.

| | |
|---|---|
| ***A61N 1/39*** | (2006.01) |
| ***F21V 33/00*** | (2006.01) |
| ***H02J 7/00*** | (2006.01) |

(52) U.S. Cl.

CPC ......... *A61N 1/3968* (2013.01); *A61N 1/3904* (2017.08); *A61N 1/3975* (2013.01); *F21V 33/0068* (2013.01); *H02J 7/0045* (2013.01)

(58) Field of Classification Search

CPC .. A61N 1/3968; A61N 1/3904; A61N 1/3975; F21V 33/0068

See application file for complete search history.

(56) References Cited

U.S. PATENT DOCUMENTS

| | | | | |
|---|---|---|---|---|
| 2017/0012448 | A1* | 1/2017 | Miller | H02J 7/342 |
| 2017/0157415 | A1* | 6/2017 | Horseman | G16H 40/63 |
| 2017/0245567 | A1* | 8/2017 | Fathollahi | H02J 7/342 |
| 2017/0271892 | A1* | 9/2017 | Cross | H02J 7/0021 |
| 2018/0169426 | A1* | 6/2018 | Montague | G16H 80/00 |
| 2018/0369599 | A1* | 12/2018 | Smith | F16M 11/10 |
| 2019/0036359 | A1* | 1/2019 | Smith | H02J 7/35 |

* cited by examiner

*Primary Examiner* — Eric D. Bertram

(74) *Attorney, Agent, or Firm* — Gurr Brande & Spendlove, PLLC; Robert A. Gurr

(57) ABSTRACT

A multi-function portable automated external defibrillator (referred to herein as "multi-function AED") comprises a housing and AED cables. The housing includes a power source that delivers a defibrillation of a set number of joules via monophasic or biphasic options. The housing may be lightweight and compact. The housing further comprises a plurality of ports, such as a charging port, a plurality of USB ports, a cable output port, a 12V port, and an AC in port. The housing also comprises a power button and a flashlight. A user may use a phone application and connect to the multi-function AED through connecting physically via the user's own phone cord or via a wireless connection to recognize and treat ventricular fibrillation.

3 Claims, 12 Drawing Sheets

116
108
106
102
100
104
103B
103A

MULTI-FUNCTION PORTABLE AUTOMATED EXTERNAL DEFIBRILLATOR

CROSS-REFERENCE TO RELATED APPLICATIONS

This application claims the benefit of U.S. Provisional Application Ser. No. 62/848,204 filed on May 15, 2019, which is incorporated herein by reference.

TECHNICAL FIELD

The present disclosure relates to an automated external defibrillator ("AED"). More particularly, the present disclosure relates to a compact multi-functional AED that functions as an AED device and battery charger, among others.

BACKGROUND

According to the World Health Organization, cardiovascular diseases ("CVDs") are the number one cause of death in the world. More people die annually from CVDs than any other cause. For example, 17.9 million people died from CVDs in 2016, which represented 31% of all deaths in the world that year. A majority of CVDs take place in developing countries and the technology that can help them cannot be easily accessed within their countries.

Currently, AEDs are expensive and are quite large and bulky, making them highly inconvenient to own and use—especially for those in low- or moderate-income categories. Due to the size and singular functionality of AEDs, they are also very uncommon for emergency use by individuals. As a result of the high cost and large size, the average person does not carry or transport AEDs. Because of these barriers, AEDs are frequently unavailable during the crucial first 8-10 minutes of cardiac events. This lowers the chance of survival significantly. In particular, it has been shown that a victim's chance of survival is reduced by 7-10% with every minute that passes without CPR and fibrillation.

Even if the high cost and size were not a factor, understanding AEDs and how the heart functions can be difficult. The layperson may not have the training that most emergency personnel have to properly use an AED Accordingly, during an emergency situation, many users will not be able to properly use the AED. In addition, AEDs are usually only used as a defibrillator. A machine, such as the AED, that has a single function may receive minimal use, thereby creating a lack of familiarity with the AED. Additionally, because AEDs in the art only have one use, it can be difficult to justify the purchase by laypeople.

Accordingly, there is a need for an AED that can be automated, easily used by a user during an emergency, is compact, inexpensive, and has multiple uses, such as a phone battery charger, car battery jumpstart device, roadside hazard lights, to name a few. The present disclosure seeks to solve these and other problems.

SUMMARY OF EXAMPLE EMBODIMENTS

In one embodiment, a multi-function portable automated external defibrillator (referred to herein as "multi-function AED") comprises a housing and AED cables. The housing includes a power source that delivers a defibrillation of a set number of joules via monophasic or biphasic options. The housing may be lightweight and compact. The housing further comprises a plurality of ports, such as a charging port, a plurality of USB ports, a cable output port, a 12V port, and an AC in port. The housing also comprises a power button and a flashlight or hazard light. Further, a user may use a multi-function AED phone application and connect to the multi-function AED through either wired or wireless connections, which aids in recognizing and treating ventricular fibrillation. The multi-function AED further comprises AED cables with ECG coupling sites for ECG pads. The AED cables can be removably attached to the cable output port.

In one embodiment, a multi-function AED may comprise battery jumper cables.

In one embodiment, a method of using a multi-function AED comprises a user utilizing a smartphone and a multi-function AED phone application. The user connects the smartphone to the multi-function AED wirelessly or by cable (e.g., USB). The user then places ECG pads on a patient's chest. Once the ECG pads are on the patient's chest, the phone application immediately calls 911 and guides the user through proper safety steps, unless in test mode. The phone application then searches for a rhythm. If a rhythm is recognized, the phone application gives safety instructions to the user on how to proceed. If the appropriate abnormal rhythm is detected, a shock is deemed necessary. The user delivers a shock of a set number of joules through the phone application to the AED in a monophasic or biphasic option. If a normal rhythm is found, or the patient has no heart rhythm and is in asystole, then no shock is performed.

DETAILED DESCRIPTION OF EXAMPLE EMBODIMENTS

Figure 1:
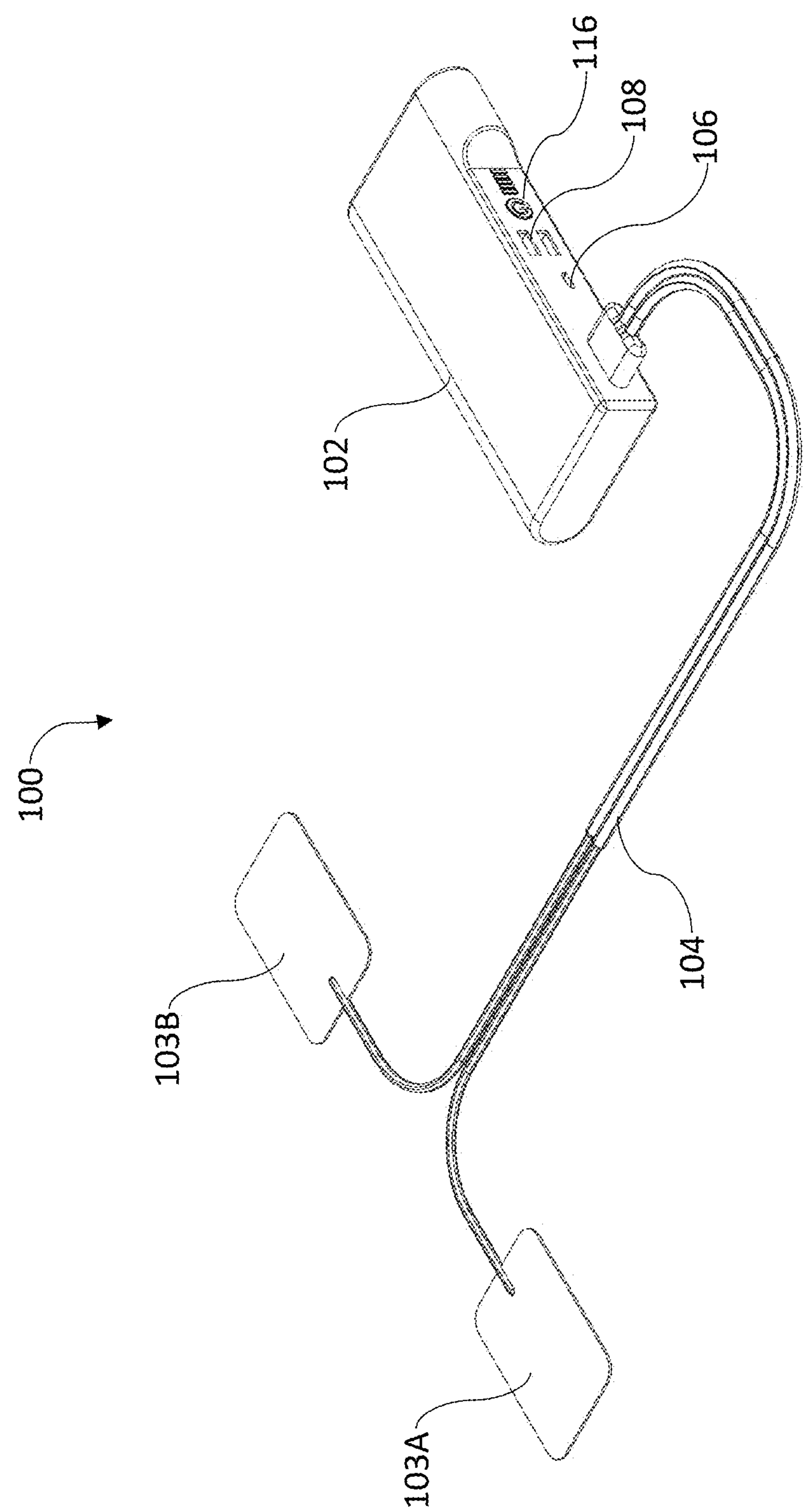
FIG. 1 illustrates a top, rear perspective view of a multi-function AED with AED cables coupled thereto.
Figure 2:
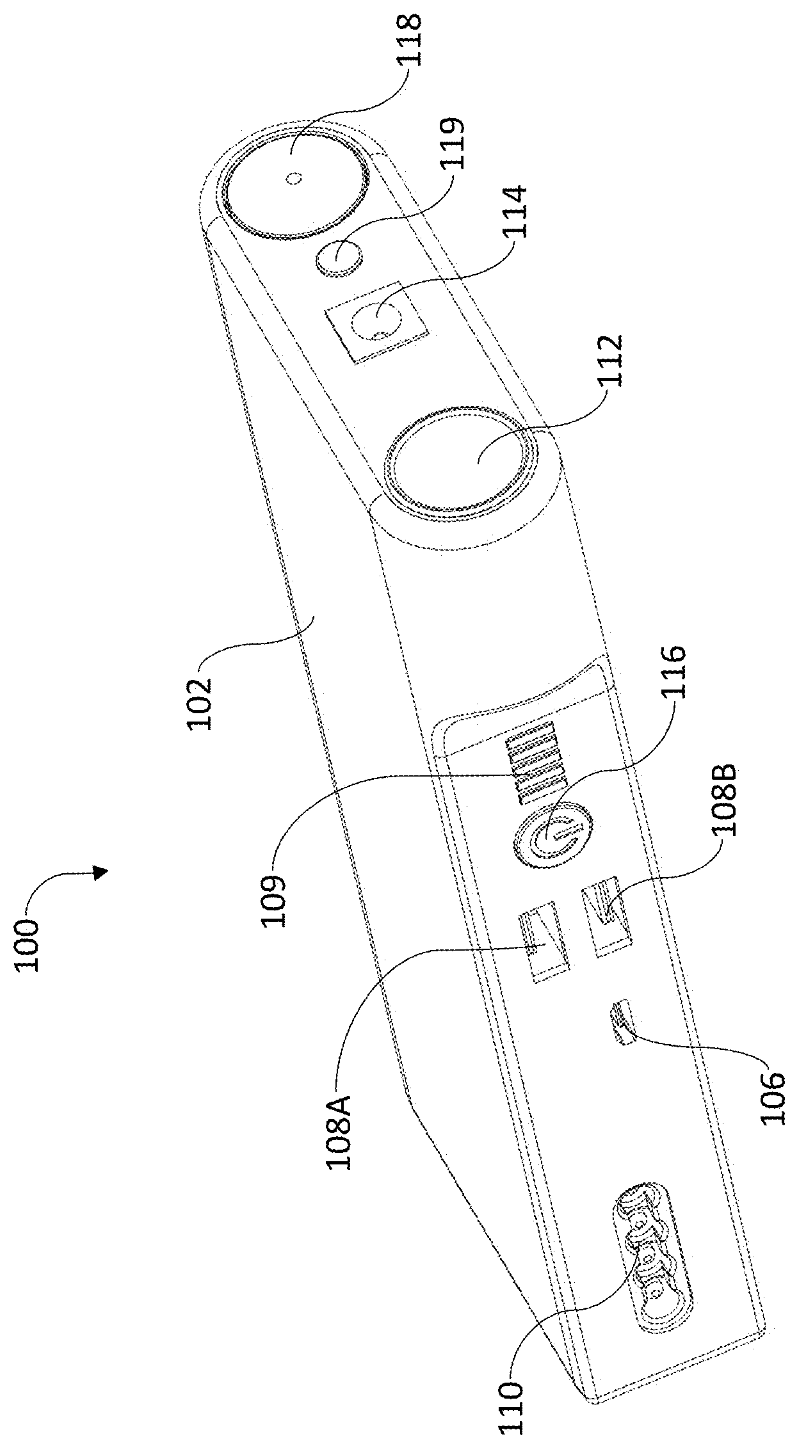
FIG. 2 illustrates a front, side perspective view of a multi-function AED.
Figure 3:
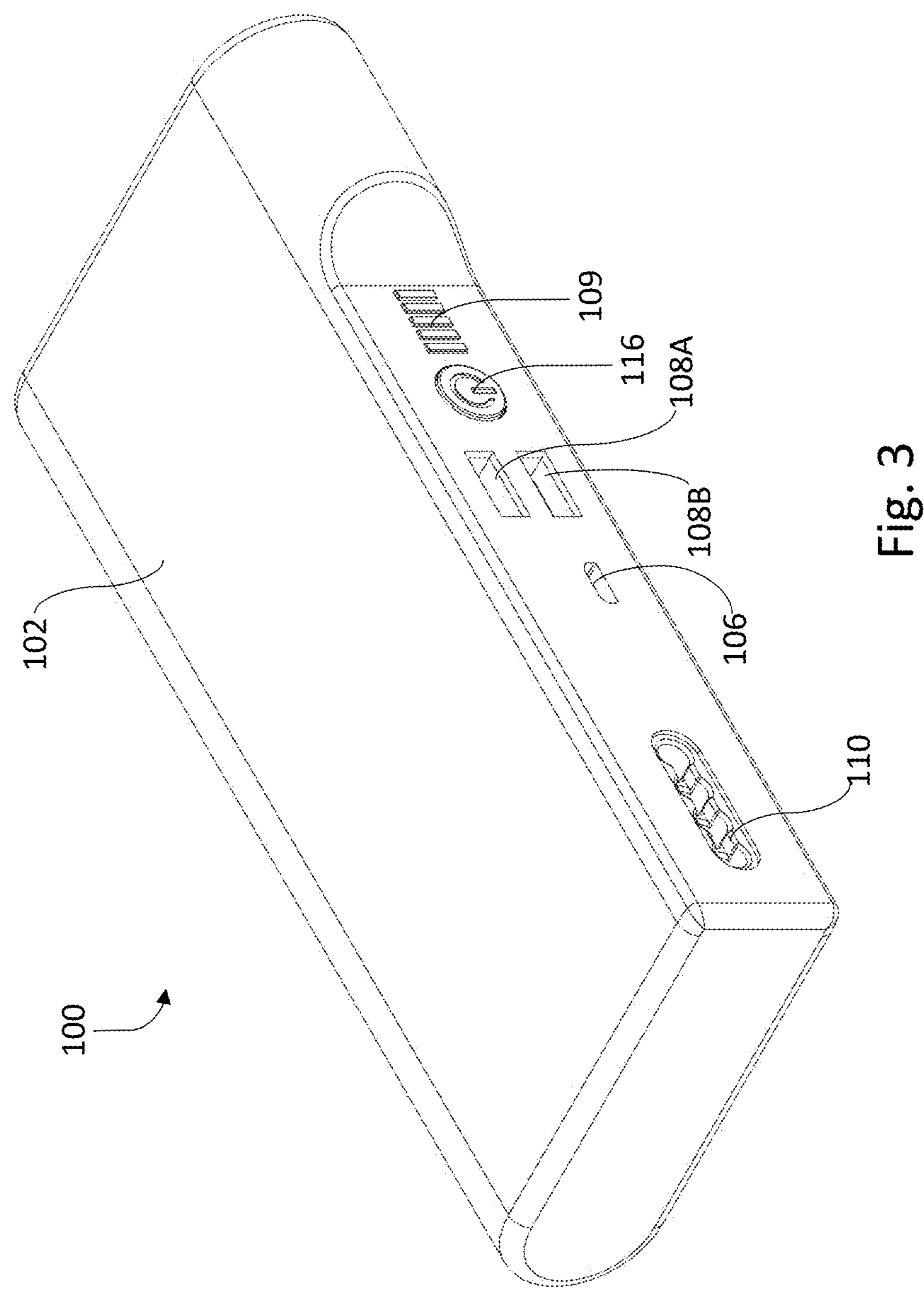
FIG. 3 illustrates a rear, top perspective view of a multi-function AED.
Figure 4:
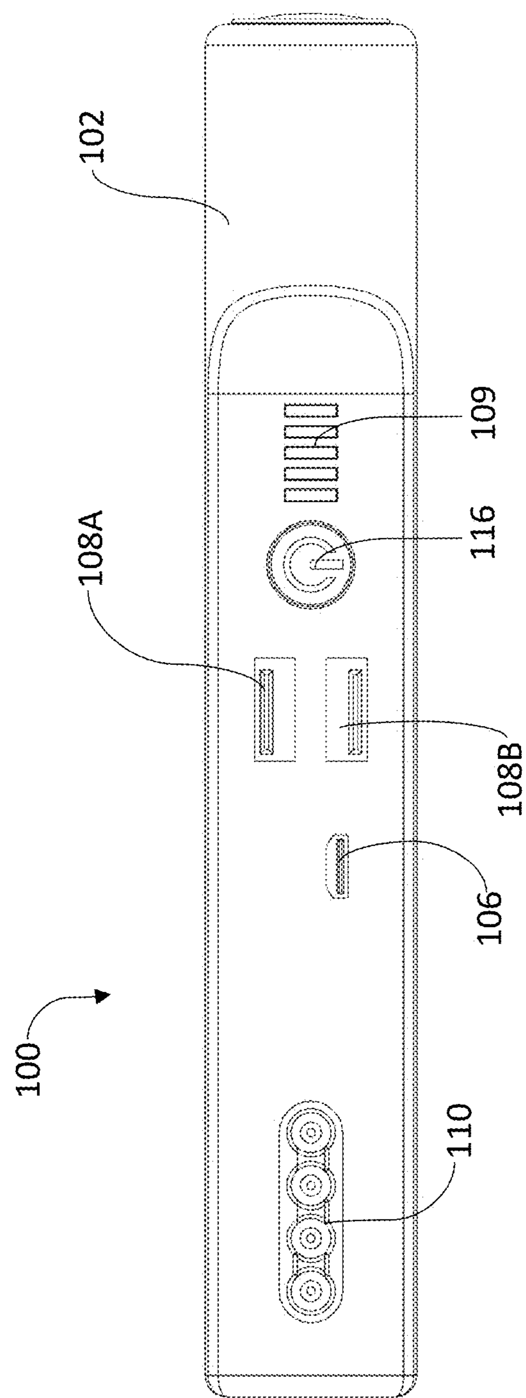
FIG. 4 illustrates a side elevation view of a multi-function AED.
Figure 5:
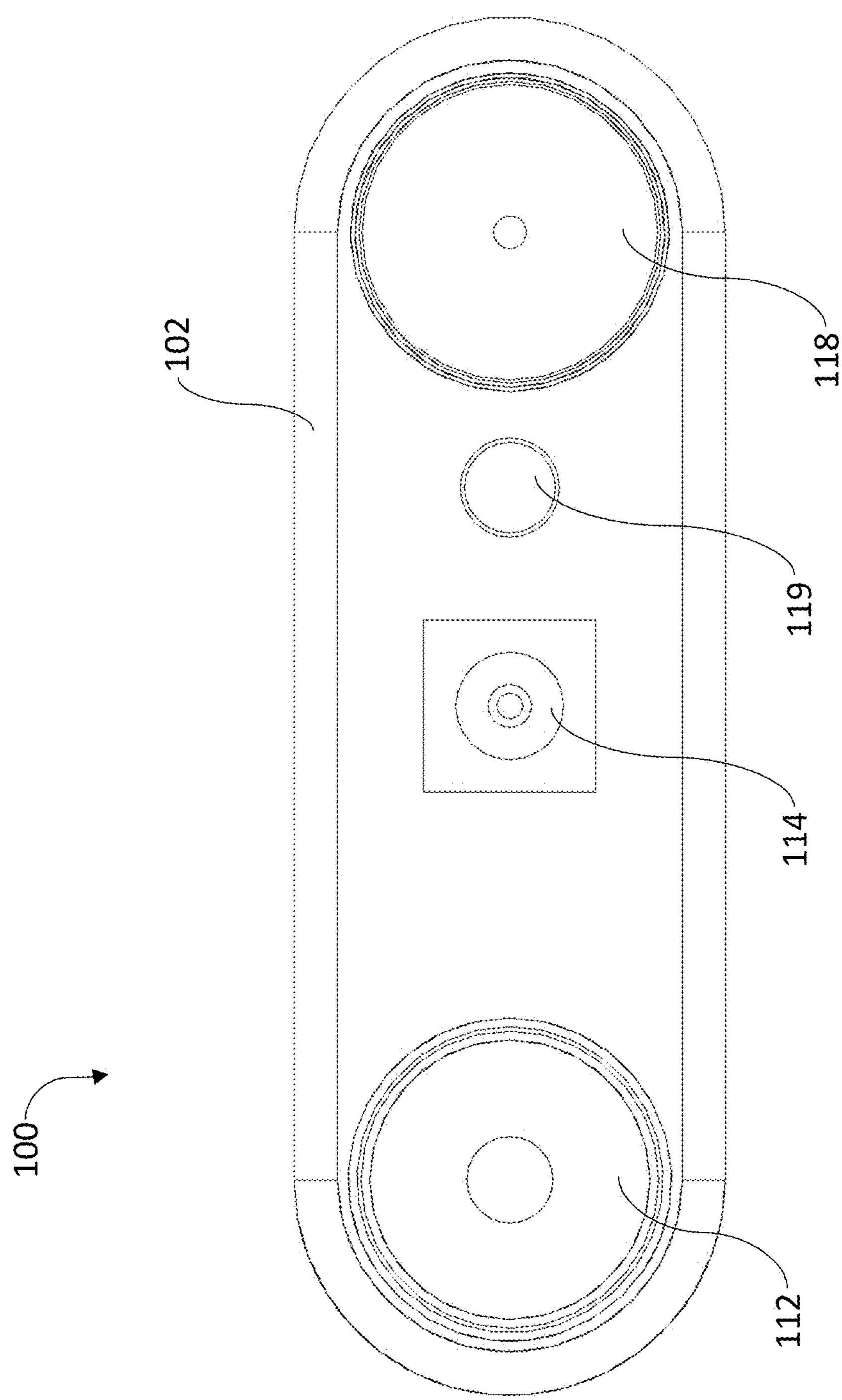
FIG. 5 illustrates a front elevation view of a multi-function AED.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As previously discussed, there is a need for an AED that can be automated, easily used by a user during an emergency, is compact, inexpensive, and has multiple uses, such as a phone or car battery charger. As will be appreciated, the multi-function AED disclosed herein solves these problems and others.

Many AEDs are present on the market. However, they are often inaccessible for the average person, especially those in the low- and middle-income categories. Not only are they expensive to obtain, but they are bulky, inconvenient, and difficult to use. On the other hand, the multi-function AED disclosed herein comprises a housing that is compact, lightweight, and user friendly, with numerous ports to charge phones and other batteries. The housing is small enough that any individual could easily carry it from destination to destination. Further, the multi-function AED comprises AED cables, which are used to deliver a monophasic or biphasic shock to a patient. To operate the multi-function AED, a user connects a phone, via a multi-function AED phone application, to the multi-function AED The multi-use AED phone application explains, in a step-by-step process, how to operate the multi-function AED. In particular, the user is directed as to whether a patient needs to be shocked. The strength of the shock will be predetermined by the device and the phone software. In addition, the multi-use AED may be used as a light, an emergency roadside light, an electronic device battery charger, and may even be used to jump a car battery.

As shown in FIG. 1, in one embodiment, a multi-function AED 100 comprises a housing 102 and AED cables 104. The housing 102 includes a power source that delivers a defibrillation of a set number of joules via monophasic or biphasic shocks via the cables 104 to a patient via patient contact pads 103A, 103B. The housing 102 is ideally compact and made from a lightweight material. While the housing 102, as illustrated, is compact and rectangular in shape, it will be appreciated that the housing 102 may be in a different formfactor and may also be larger for other settings, such as where the multi-function AED is stationary or in a commercial or institutional setting.

As shown in FIGS. 2-5, the housing 102 further comprises a plurality of ports, such as a charging port 106, USB ports 108A, 108B, a cable output port 110, a 12V port 112, and an AC port 114. While the above ports are illustrated, it will be appreciated other ports can also be used in combination with, or in lieu of, the above-mentioned ports, such as micro USB, USB-C, Apple® ports, or any other electronic port known in the art. It will further be appreciated that there may be more or less ports than those illustrated. The housing 102 also comprises a power button 116 and a flashlight 118 (which can also be a hazard light), which is illuminated via a light switch 119. The power button 116 activates the multi-function AED. The power button 116 may be a push button, as illustrated, or, for example, a switch, a moveable dial, or other button/switch.

The USB ports 108A, 108B may be used for phone charging and charging any compatible electronic device. Specifically, the multi-function AED 100 can act as a portable charger that can be used in daily situations or on vacations where other means of charging are not accessible for a phone or other electronic devices. The AED in the prior art is a single-function AED, which is to purely be a defibrillator. In contrast, the multi-function AED 100 is not limited to just one function and can be used for daily activities. With the amount that the American population relies on their smart devices, constant charging of smart devices is common. Having a multi-function AED 100 creates ease and convenience for those looking to charge their phones while on a walk, at the park, or spending time away from places with power.

The power source of the AED 100 can be a rechargeable battery (e.g., Lithium-Ion) that is charged through a charging port 106 (e.g., a micro-USB port). However, it is not limited to a rechargeable battery. For example, it may comprise disposable batteries that must be replaced once the multi-function AED 100 ceases to function or indicates to a user that the battery is low. Further, in an alternate embodiment, the housing 102 may comprise solar panels so that in locations where power is not readily available, the multi-function AED may still be charged. It will be appreciated that the power source, with the rechargeable battery, decreases costs as well as allows the multi-function AED 100 to perform frequent self-testing and routine maintenance testing to ensure that the device is functioning properly. The multi-function AED 100 can potentially communicate with the user's smart phone or tablet to notify them when the battery has reached a point it needs to be charged.

In contrast, the prior art AED can be difficult to maintain because of the limited battery storage as well as infrequent professional maintenance. In particular, self-tests on typical AEDs drain batteries and force the user to continually check the battery level. This can produce a dangerous situation due to the fact that the prior art AED may not have sufficient power to produce a life-saving jolt if the batteries are not charged. The multi-function AED 100 utilizes a power source that can be quickly recharged so that in case of an emergency, it will be ready to function properly. In one embodiment, the AED 100 may comprise one or more charge indicators 109 (e.g., plurality of Light Emitting Diodes) so that a user is aware how much power remains, and, particularly, if the battery level is above a threshold capable of producing the life-saving jolt. For example, a threshold indicator may include a physical line between LEDs, a certain color of LEDs, or other method of indicating the threshold required for defibrillation. This can potentially be communicated with the user through their smart phone or tablet.

Figure 6:
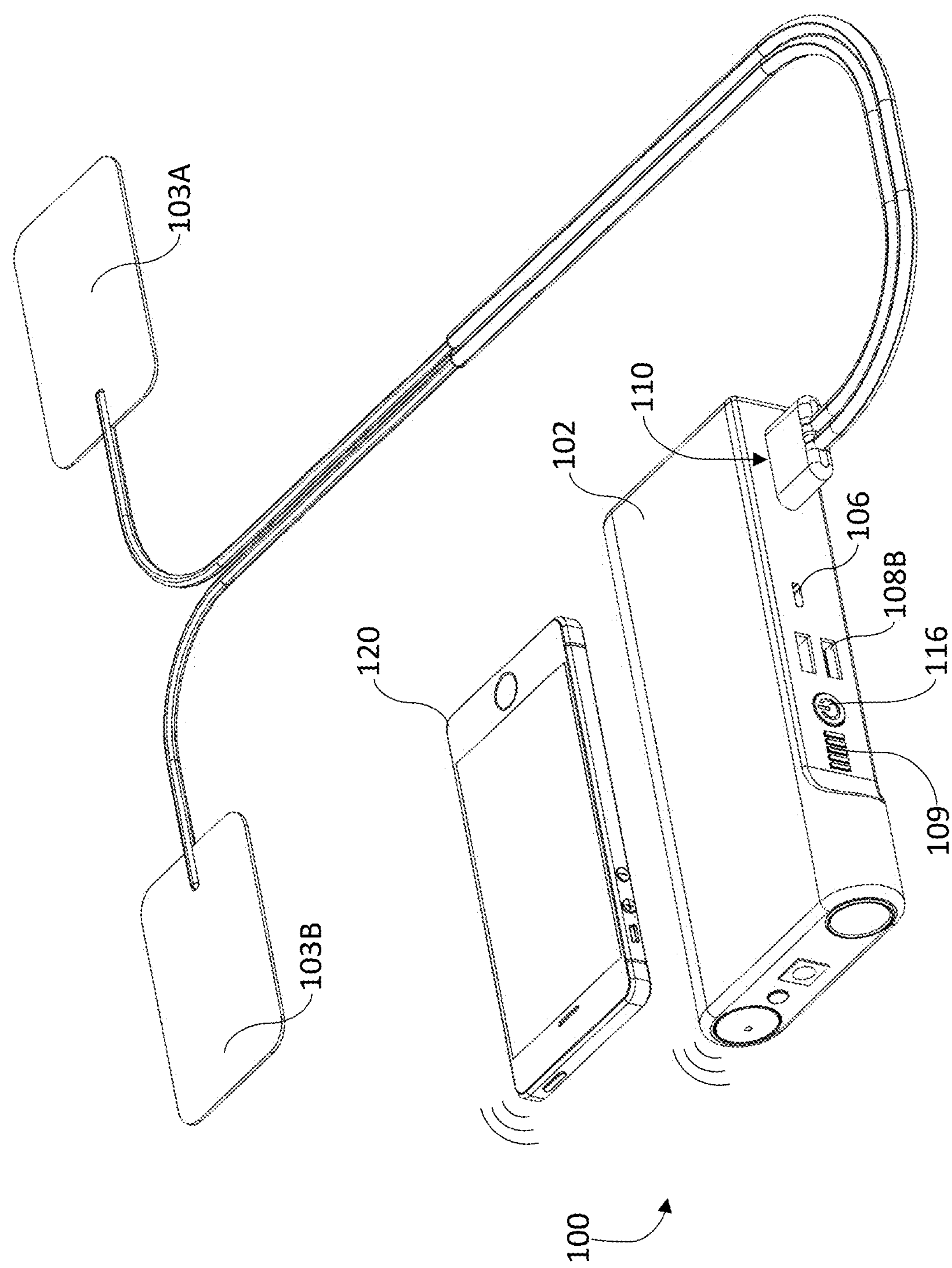
FIG. 6 illustrates a top, front perspective view of a multi-function AED with AED cables coupled thereto and a smartphone.

As shown in FIG. 6, a smartphone 120, with a multi-use AED phone application installed thereon, is used in conjunction with the multi-function AED 100, which allows a user to access instructions and control the multi-function AED 100. A user may use the phone application and connect to the multi-function AED 100 through wired or wireless connections, such as Bluetooth® or WiFi®, to recognize and treat ventricular fibrillation. In such a scenario, the AED 100 may rely on the processors within the phone, thereby reducing the cost and increasing the efficiency of the AED 100. However, in other embodiments, the AED 100 may comprise microcontrollers or other processors capable of performing these functions without a smartphone. In such a scenario, the AED may further comprise a display to alert a user to steps. Referring back to FIG. 6, the multi-function AED 100 further comprises AED cables 104 (shown in FIGS. 1 and 6) with patient contact pads 103A, 103B (e.g., ECG pads).

Further, the AED cables 104 may be of a variety of lengths. For example, a short AED cable 104 may be used to create a more compact multi-use AED 100. The AED cables 104 can be removably attachable to the cable output port 110. As the AED cables 104 are removably attachable from the cable output port 110, it will be appreciated that other cables or systems can also utilize the same cable output port 110. It will further be appreciated that the AED cables 104 may utilize a different port than the cable output port 110. For example, the AED cables 104 may utilize the 12V port 112, a USB port 108A-B, or any other port capable of outputting the necessary power for defibrillation.

Figure 7:
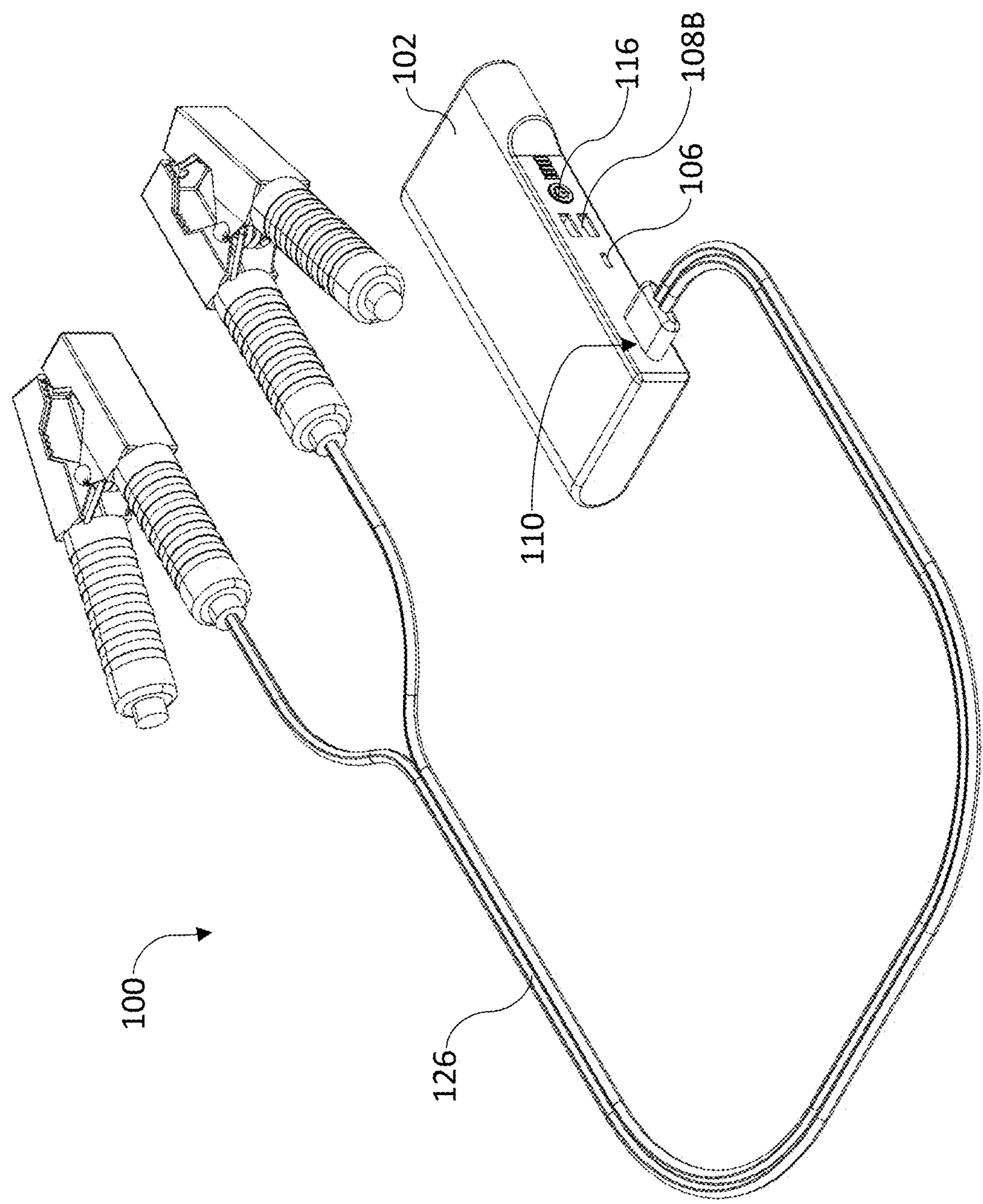
FIG. 7 illustrates a top, rear perspective view of a multi-function AED with jumper cables coupled thereto.

As shown in FIG. 7, in one embodiment, a multi-function AED 100 may comprise battery jumper cables 126. The jumper cables 126 may couple to the cable output port 110 in place of the AED cables 104. Being able to use the multi-function AED 100 frequently and in many ways, such as to jump a car battery, allows a user to become familiar with the device so that the device can be comfortably used in any emergency situation. In contrast, the prior art AED is rarely used due to its cost and singular functionality. Further, the cost and singular functionality prevents it from being in the hands of many people, and the lack of having an AED with multiple functions can create a lack of familiarity.

In one embodiment, a method of using a multi-function AED 100 comprises using a smartphone 120, with a heart rhythm recognition phone application installed, to connect to the multi-function AED either wirelessly or by cable. The user then places ECG pads 103A, 103B on a patient's chest. Once the ECG pads 103A, 103B are on the patient's chest, the phone application immediately dials 911 and guides the user through proper safety steps, unless in test mode. The phone application then searches for a shockable rhythm (e.g., ECG pads 103A, 103B receive signals from the body that are transmitted to a microcontroller, the phone in communication with the microcontroller via a Bluetooth® transceiver). If a heart rhythm is recognized, the phone application gives safety instructions to the user on how to proceed. If the appropriate abnormal rhythm is detected, a shock is deemed necessary. The user delivers a shock of a set number of joules through the phone application to the AED 100 in a monophasic or biphasic option via the cables 104 and ECG pads 103A, 103B. If a normal rhythm is found, or the patient has no heart rhythm and is in asystole, then no shock is performed.

In another method of use, a user couples the jumper cables 126 to the power output port 110. A user may then connect the jumper cables 126 to a car battery. The AED 100 may then be used to jump the car battery using a smartphone application or using an input directly on the AED 100, such as power button 116 or other button used for jumping a battery.

Figure 8:
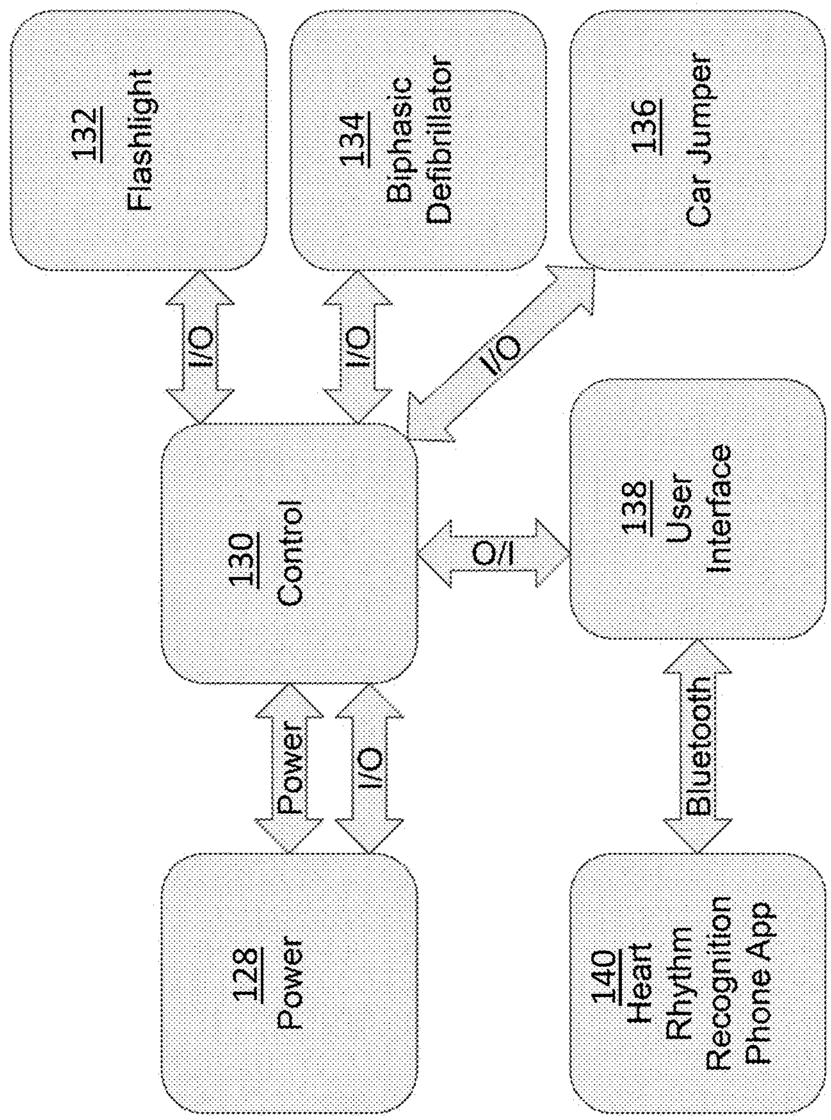
FIG. 8 illustrates a block diagram of a multi-function AED.

As illustrated in the multi-function AED block diagram of FIG. 8, power 128 sends power and input/output (I/O) to a controller 130 (e.g., microcontroller or other processor). The controller 130 has I/O between a flashlight 132, a biphasic defibrillator 134, a car jumper 136, and user interface 138. Further, the user interface 138 communicates with a heart rhythm recognition phone app 140, ideally through Bluetooth® or other wireless connection.

Figure 9:
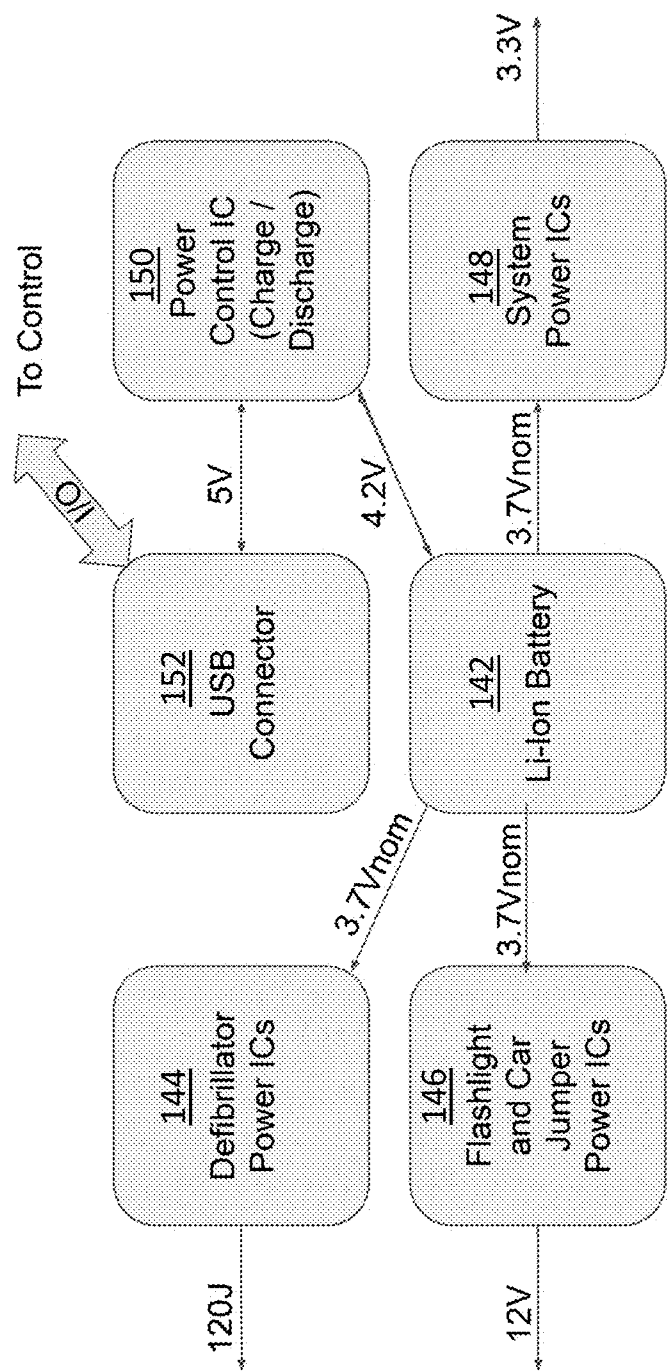
FIG. 9 illustrates a block diagram of a power supply of a multi-function AED.

The block diagram of FIG. 9 illustrates the power distribution (power 128 in FIG. 8) of the multi-function AED 100. As used herein, "IC" means Integrated Circuit. As shown, a Lithium-Ion Battery 142 within the housing 102 is capable of outputting 1) 3.7 Vnom (battery's nominal voltage) to a Defibrillator IC 144, which is capable of producing 120 J of power; 2) 3.7 Vnom to a an IC 146 for the flashlight and car jumper, capable of producing 12V; 3) 3.7 Vnom to a System Power IC 148 capable of producing 3.3V; and 4) 4.2V to a Power Control IC (Charge/Discharge) 150 that can produce and receive 5V of power from a USB connector 152, which is capable of input/out with the controller 130.

Figure 10:
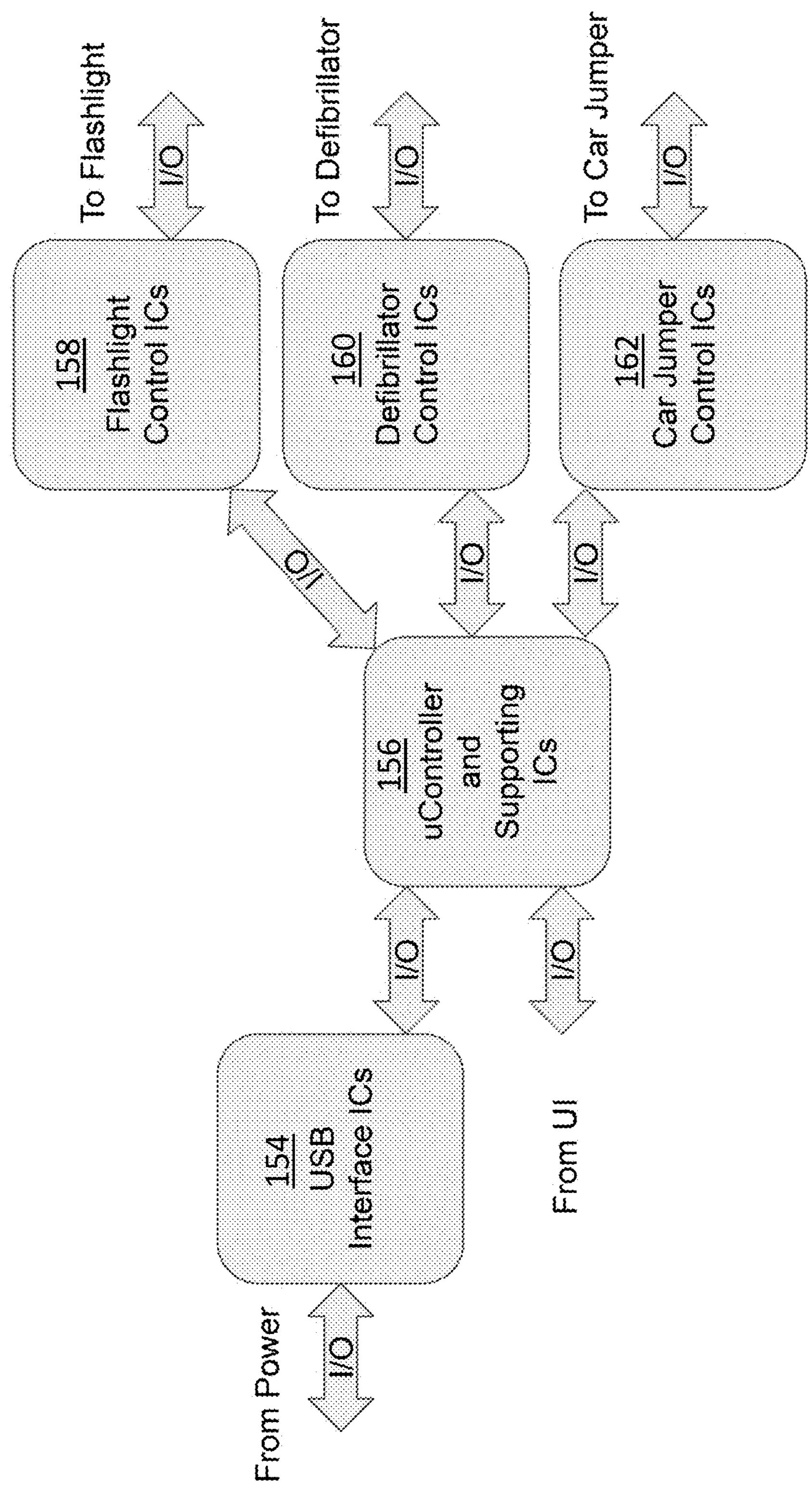
FIG. 10 illustrates a block diagram of a control system of a multi-function AED.

As shown in the control block diagram of FIG. 10 (control 130 in FIG. 8), there is I/O from power 128 (FIGS. 8-9) to a USB Interface IC 154. Then there is I/O between a microcontroller and supporting ICs 156 and the USB Interface ICs 154. Also, there is I/O between the microcontroller and supporting ICs 156 and a Flashlight Control ICs 158, Defibrillator Control ICs 160, and Car Jumper Control ICs 162. The Flashlight Control ICs 158 have I/O to the Flashlight, the Defibrillator Control ICs 160 have I/O to the Defibrillator, and the Car Jumper Control ICs 162 have I/O to the Car Jumper. Lastly, the microcontroller and supporting ICs 156 has I/O from User Interface 138, which may include a smartphone.

Figure 11:
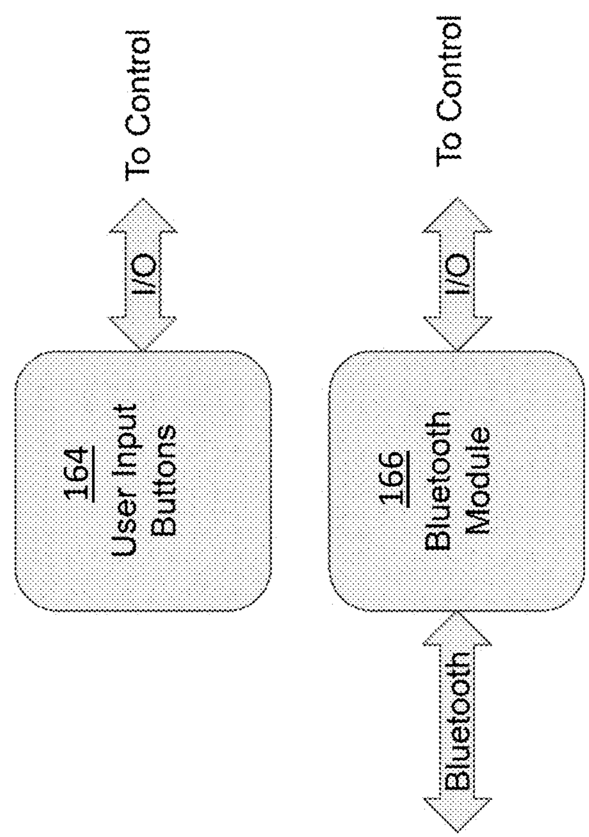
FIG. 11 illustrates a block diagram of a user interface of a multi-function AED.

FIG. 11 illustrates a block diagram of a user interface. The User Input Buttons 164 (e.g., light switch 119) have I/O to Controller 130 (shown in FIG. 8). Bluetooth® signals (or other wireless or wired signals), such as from a phone or other smart device, may be received and/or delivered by a wireless transceiver 166 (e.g., Bluetooth module 166) where there is I/O between the Bluetooth Module 166 and Controller 130.

Figure 12:
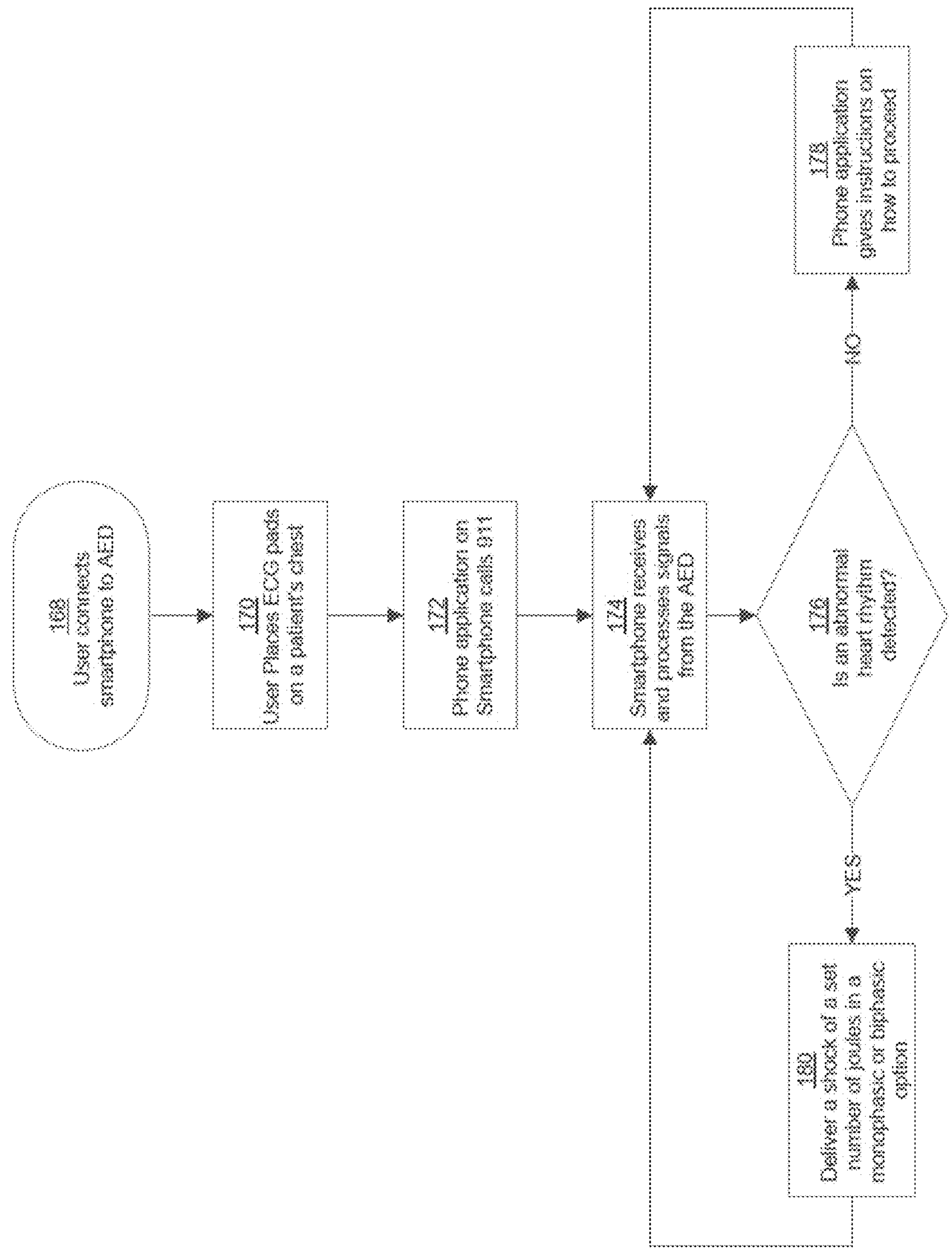
FIG. 12 is a flow chart of one method of using the multi-function AED.

As shown in the flow chart of FIG. 12, at start 168, a user connects a smartphone to the AED 100. At step 170, the user places ECG pads on a patient's chest. At step 172, the phone application on the smartphone calls 911. Then, at step 174, the smartphone receives and processes signals from the AED 100. In step 176, it is determined if an abnormal heart rate rhythm detected. If the heart rate is normal or there is no heart rate, then at step 178, the phone application gives instructions on how to proceed and then returns to step 174. If an abnormal heart rate is detected, then at step 180, the AED 100 delivers a shock of a set number of joules in a monophasic or biphasic option. After the shock has been delivered, return to step 174.

As understood from the foregoing, the multi-function AED 100 functions as a car battery jumper, a battery bank, and a smaller, more compact and portable AED than is currently available in the art. This allows for more frequent use and greater chance of availability. By combining the multi-function AED 100 with smartphone capabilities and the smartphone application, the overall cost of the multi-function AED 100 is reduced by eliminating hardware and software components on the multi-function AED 100 itself, allowing it to be more cost-effective for a user.

While specific voltages are shown and described herein, the multi-function AED 100 is not so limited. Indeed, variations from these voltages are contemplated herein and fall within the scope of the invention.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A multi-function automated external defibrillator comprising:
- a housing;
- a plurality of ports comprising:
  - a charging port,
  - a USB port,
  - a cable output port,
  - a 12V port, and
  - an AC port;
- a lithium-ion battery configured to output 3.7Vnom to a defibrillator power integrated circuit for outputting 120 J to a patient, and 3.7Vnom to a flashlight and car jumper integrated circuit for outputting 12V to jumper cables;
- a wireless transceiver;
- a controller;
- AED cables, comprising ECG pads, removably attachable to the cable output port;
- vehicle jumper cables removably attachable to the cable output port; and
- a multi-function AED phone application executable on a smartphone, the smartphone wirelessly coupled to the wireless transceiver, the multi-function AED phone application configured to:
  - i. when the AED cables are coupled to the output port:
    - a. dial 911 when the ECG pads are placed on a user; and
    - b. if no heartbeat is detected or an abnormal heartbeat is detected, send a signal to the controller, via the wireless transceiver, to deliver a shock to the user of a predetermined number of joules; and
  - ii. when the vehicle jumper cables are coupled to the output port;
    - a. send a signal to the controller, via the wireless transceiver, to deliver a predetermined number of joules to jump a car battery.

2. The multi-function automated external defibrillator of claim 1, further comprising a flashlight.

3. A multi-function automated external defibrillator comprising:
- a housing;
- a plurality of ports comprising:
  - a charging port,
  - a USB port,
  - a cable output port,
  - a 12V port, and
  - an AC port;
- a rechargeable internal power source;
- a wireless transceiver;
- a controller;
- AED cables, comprising ECG pads, removably attachable to the cable output port;
- vehicle jumper cables removably attachable to the cable output port; and
- a multi-function AED phone application executable on a smartphone, the smartphone wirelessly coupled to the wireless transceiver, the multi-function AED phone application configured to:
  - i. when the AED cables are coupled to the output port:
    - a. dial 911 when the ECG pads are placed on a user; and
    - b. if no heartbeat is detected or an abnormal heartbeat is detected, send a signal to the controller, via the wireless transceiver, to deliver a shock to the user of a predetermined number of joules; and
  - ii. when the vehicle jumper cables are coupled to the output port:
    - a. send a signal to the controller, via the wireless transceiver, to deliver a predetermined number of joules to jump a car battery.

* * * * *